United States Patent
Miller et al.

(10) Patent No.: US 8,956,998 B2
(45) Date of Patent: Feb. 17, 2015

(54) HERBICIDAL COMPOSITIONS AND METHOD OF USE THEREOF

(71) Applicants: Lawrence A Miller, Brookfield, CT (US); Robert L Hodge, Sumter, SC (US)

(72) Inventors: Lawrence A Miller, Brookfield, CT (US); Robert L Hodge, Sumter, SC (US)

(73) Assignee: Proactive LLC, Brookfield, CT (US)

( * ) Notice: Subject to any disclaimer, the term of this patent is extended or adjusted under 35 U.S.C. 154(b) by 0 days.

(21) Appl. No.: 14/277,839

(22) Filed: May 15, 2014

(65) Prior Publication Data

US 2014/0249028 A1    Sep. 4, 2014

Related U.S. Application Data

(63) Continuation-in-part of application No. 13/726,061, filed on Dec. 22, 2012, now Pat. No. 8,815,776.

(60) Provisional application No. 61/801,662, filed on Mar. 15, 2013.

(51) Int. Cl.
  *A01N 43/36* (2006.01)
  *A01N 43/76* (2006.01)
  *A01N 33/18* (2006.01)

(52) U.S. Cl.
  CPC ............... *A01N 43/76* (2013.01); *A01N 33/18* (2013.01)
  USPC ........................................................ 504/138

(58) Field of Classification Search
  None
  See application file for complete search history.

(56) References Cited

U.S. PATENT DOCUMENTS

2009/0005249 A1 *   1/2009   Myers et al. .................. 504/138

* cited by examiner

*Primary Examiner* — Alton Pryor
(74) *Attorney, Agent, or Firm* — Hayden Stone PLLC; Christopher G. Hayden

(57) ABSTRACT

An emulsifiable concentrate herbicidal composition that contains Prodiamine herbicide and fenoxaprop-p-ethyl that shows excellent spreadability and stability and is particularly suitable for effective control of weeds in general residential and commercial landscaped areas.

18 Claims, No Drawings

HERBICIDAL COMPOSITIONS AND METHOD OF USE THEREOF

RELATED APPLICATIONS

This application claims priority to and benefit of U.S. Provisional application 61/801,662 titled HERBICIDAL COMBINATIONS AND METHOD OF USE THEREOF filed on Mar. 15, 2013. This application is also a continuation in part of U.S. application Ser. No. 13/726,061 titled Herbicidal Compositions and Methods of Use Thereof, filed on Dec. 22, 2012, the entire document of which is incorporated by reference herein for all allowable purposes.

FIELD OF THE INVENTION

The invention relates to emulsifiable concentrate formulations of prodiamine and fenoxaprop-p-ethyl, particularly formulations comprising at least 5% prodiamine and at least 1% phenoxaprop-p-ethyl, and use thereof to control undesired weeds, particularly to control crabgrass in turf. The invention also relates to manufacturing concentrates comprising at least 25% prodiamine and at least 3% phenoxaprop-p-ethyl.

BACKGROUND OF THE INVENTION

The statements in this section merely provide background information related to the present disclosure and may not constitute prior art.

Lawn care, golf courses, sod farms, athletic fields and the like all require herbicide treatments to control weeds. It is an important aspect of the herbicidal treatment that it is able to control such weeds without harming the lawn or other turf in which the weeds are found. An important consideration in treating turf is the cost, in terms of man and machine hours, cost of chemicals, and down-time of the treated surface for a variety of normal uses. Therefore, there is considerable pressure to combine various lawn treatments, including treating diseases, eliminating pests, fertilizing, and treating for weeds.

Crabgrass is a huge problem in turf. It will aid in an understanding of the present invention for those not skilled in the art, to know that the life cycle of grassy weeds occurs in stages which are very well known to those skilled in the art. There is of course the pregermination stage. After germination has begun there is a post germination stage. When the plant rises from the ground it first appears as a shoot and develops leaves. The leaf stage may be characterized by the number of leaves, e.g. 1 leaf stage, 2 leaf stage etc., and is generally characterized as leaves extending from a single shoot or stalk. As the plant matures, tillers develop which are branching, sprouts or stalks that will generally eventually develop leaves of their own. This stage of the weed growth may be characterized by the number of tillers present, such as the 1 tiller stage, the 2 tiller stage, etc. Thus, stages may be referred to for example as "the preemergence stage", the "early post germination 1-2 leaf stage", the "untillered 3-5 leaf stage" and the "tillered" stage which may further be defined as for example, as the "1 tiller stage", the "2 tiller stage", the "3+ tiller stage" and the like.

In order to control grassy weeds in lawn or turf it is known to treat such grassy weeds with preemergent herbicides. For example, with regard to grassy weeds such as crabgrass, goosegrass or other grassy weeds, it is known to treat a lawn, golf course, sod farm, athletic field or other lawn or turf setting infested with the grassy weeds early in a growing season before the grassy weed has germinated with a preemergent herbicide such as prodiamine. The use of prodiamine to control crabgrass in turf is well known. However, crabgrass continually re-seeds, so it is not possible to effectively treat established crabgrass using only prodiamine.

Fenoxaprop p-ethyl (we herein alternatively refer to the herbicide as "fenoxaprop") is a postemergence graminicide used on cool-season turfgrasses to control crabgrass and other annual grass weeds. It is available as the D isomer, the R isomer, or as mixtures. The R isomer is recognized as being more effective in some situations, and in preferred embodiments of this invention the active isomer is present and the less active isomer is only present in trace quantities. It is known to treat grassy weeds such as crabgrass, goosegrass or other grassy weeds after the weed has emerged in the lawn, golf course, sod farm athletic field or other lawn or turf setting, with a post emergent herbicide such as fenoxaprop.

There is considerable art suggesting combinations of fenoxaprop with other herbicides results in reduced fenoxaprop efficacy. See, for example, Antagonism of Fenoxaprop by Broadleaf Herbicides (Harrison, 1987), stating that the herbicidal action of fenoxaprop is significantly reduced when applied within several days of or in combination with various postemergence broadleaf herbicides, resulting in unacceptable levels of grassy weed control. See also Fenoxaprop Activity Influenced by Auxin-like Herbicide Application Timing (Dernoeden and Fidanza, HortScience 29 (12), 1994), stating smooth crabgrass control by fenoxaprop was reduced significantly when the broadleaf weed herbicide was applied up to 14 days or less before fenoxaprop was applied.

That said, it is also known to combine post-emergent fenoxaprop with various pre-emergent herbicides to achieve enhanced control of crabgrass. See, for example, Fenoxaprop Combined with Preemergence Herbicides for Crabgrass and Goosegrass Control in Turf (Dernoeden, HortScience 23 (1), 1988). which noted when fenoxaprop was applied in combination with bensulide, beefin, DCPA, oxadiazon, pendimethalin, or prodiamine, excellent (90% to 100%) season-long smooth crabgrass control was achieved. In this work, fenoxaprop and prodiamine were tank mixed or applied separately, at rates of 0.28 and 0.39 kg/ha fenoxaprop plus 1.1 kg/ha prodiamine. The combination treatments provided greater crabgrass control than did treating with fenoxaprop alone at identical application rates.

This enhanced control provided by applications of prodiamine and fenoxyprop is known in the industry. Labels commonly suggest using lawn treatments of prodiamine and fenoxyprop. For example, the label for ACCLAIM™ EXTRA brand fenoxaprop states Acclaim Extra is useful at rates of 9.0 to 28 fluid ounces/acre . . . when tank mixing with the following products: Barricade®, bensulide 4E, Dacthal®, Dimension®, pendimethalin, Tupersan® and Ronstar® WP. Barricade® is a prodiamine formulation.

There are co-formulations of fenoxyprop and pendimethalin. AGR40500 3.09EC contains 1 part fenoxyprop p-ethyl to 34 parts pendimethalin. Testing of this formulation is described in Crabgrass Control With a Fenoxaprop/Pendimethalin Co-Formulation—1995 Results (J. Thomas and D. Spak, p 122), which found no significant difference in treatments with a 1:25 co-formulation versus the available 1:34 fenoxyprop/pendimethalin ratio.

Despite the common practice in the industry of when drafting patent applications, stating a new herbicide can be used with large random lists of herbicides, there are no commercially available formulations of prodiamine with fenoxaprop. Prodiamine is very difficult to formulate into emulsifiable concentrates, and the presence of other herbicides typically results in unstable formulations. It is known to mix solid prodiamine formulations with certain other herbiocides. US 20120108429 describes a granule having a surface and a core; a dicarboximide herbicide such as flumioxazin adhered to the surface or mixed into the core, and a dinitroaniline herbicide such as is trifluralin or prodiamine adhered to the surface or mixed into the core. In described embodiments the granules contained 0.125% total weight percent of flumioxazin, prodiamine, or trifluralin. And one reference, US 20100279865, taught a herbicidal composition comprising a mixture of glyphosate, diquat, prodiamine, and ammonium sulfate. In these formulations, 0.125% prodiamine is dissolved into iso-paraffins, and then admixed into a slurry containing surfactants and ammonium sulfate.

Emulsifiable concentrate (EC) formulations are a favored liquid delivery system for agriculturally active compounds. Conventional EC's contain one or more active ingredients dissolved in a water immiscible solvent together with emulsifying surfactants. These solvents typically have very low solubility in water and have a high solubility for most agriculturally active compounds.

The presence of the solvent imparts significant advantages to the formulation, such as a higher degree of systemicity, which leads to higher overall biological activity as compared to other commonly used agricultural formulations such as wettable powders (WP), water dispersible granules (WDG) or suspension concentrates (SC). Such EC's are further easier to transport and store.

Some major differential properties that lead to the better efficacy, stability and easier commercial use for EC's versus SC's may be described as; EC's are true solutions vs SC's which are suspensions, EC's are thermodynamically stable vs kinetically stable SC's, EC's have a much smaller particle size (<1 nm vs 2-5 um), the primary stabilization force for EC's is solution energy which is much greater than electrostatic and steric energy for SC's, and the lower intrinsic viscosity of EC's leads to Newtonian flow which is a key factor in non-clogging and even spread of herbicide during commercial sprayings.

A good EC is not made using a simple formula that is transferable from active ingredient to active ingredient. It requires the formation of a stable emulsion upon dilution with water that does not separate upon standing.

Several publications describe the development of herbicidal emulsifiable concentrates. More specifically towards the embodiments in the present invention, select publications have attempted to form or improve the emulsion properties of low solubility herbicides such as the dinitroaniline class of compounds, in which Prodiamine can be loosely placed. For example, WO 98/48624 shows the improvement of the stability of the EC emulsion by the use of a high amount of a water-insoluble C6-C18 alkyl pyrrolidone. However, these compounds are highly corrosive, have significant phytotoxicity and are too expensive for use in many agricultural applications. U.S. Pat. No. 5,035,741 shows the use of fatty acids in the formulation of emulsifiable concentrates to improve the herbicidal activity of some compounds. U.S. Pat. No. 5,270,286 describes the formulation of a combination of imidazolinone and dinitroaniline herbicides as emulsifiable concentrates with the use of aromatic solvents and alkyl phenol polyethylene oxide condensates to improve solubility. US 20100279865 describes the formulation of a combination of many herbicides with Prodiamine in which ammonium sulfate is used to stabilize the colloidal solution and an oil soluble solvent is specifically excluded, due to the solubilization difficulties inherent in these molecules. US 2011281731 describes the formation of an emulsifiable concentrate of dinitroaniline herbicides that avoids crystallization at low temperature and which comprises a diester co-solvent having the following formula R1OOC—(CH2)n-COOR2. US 2005113253 and JP7109193 describe fertilizer compositions that contain Prodiamine but specifically do not describe the potential use of an EC formulation to achieve a superior composition.

These and other publications in the prior art, describe the inherent difficulty in producing a commercially viable EC formulation and may be instructive for the absence of a commercial EC formulation containing Prodiamine herbicide as the primary active ingredient. Further, none of the above publications provides for a method to produce a stable, low phytotoxic, environmentally friendly emulsifiable concentrate formulation of Prodiamine, which can be used, directly or indirectly, for superior weed control.

Despite the desirability of applying fenoxaprop with prodiamine, there is no combination fenoxaprop/prodiamine emulsifiable concentrate on the market. Even recent work on the combination, for example US 20090005249 which was directed toward a combination of fenoxaprop and prodiamine, tank-mixed separate concentrates. US 20090005249 teaches "the fenoxaprop and the prodiamine may be mixed by admixing liquid solutions of the two, by admixing separate granules of the two and/or by providing granules which include both prodiamine and fenoxaprop on or impregnated within the granule." When using three herbicides, the application states "the fenoxaprop, the prodiamine and the three-way herbicidal may be mixed by admixing liquid solutions of the three, by admixing separate granules of the three and/or by providing granules which include all three of prodiamine, fenoxaprop and the three-way herbicidal composition on or impregnated within the granule."

While US 20090005249 does teach that fenoxaprop and prodiamine may be both present in a granule, it does not teach a liquid concentrate comprising both. For formulating the liquid solutions, both the text and the examples teach tank mixing—the same art that was used in the 1985 studies.

What is needed is an emulsifiable concentrate solution containing fenoxaprop and prodiamine.

SUMMARY OF THE INVENTION

Emulsifiable concentrates of prodiamine and fenoxyprop are not available. No one has formulated a concentrated EC containing both prodiamine and fenoxyprop, despite the obvious desirability of combining the ingredients. Fenoxyprop shows excellent solubility in aromatic solvents, but such solvents are poor for use with prodiamine. Formulating a stable concentrated EC containing compounds with such marked solubility characteristics, including selecting appropriate adjuvants especially including the surfactants, has not been done.

The invention is the formulation and use an emulsifiable concentrate solution comprising, or alternatively consisting essentially of, the active ingredients fenoxaprop and prodiamine, one or more solvents selected from herein-listed polar aprotic solvents, and other adjuvants as described herein. By "consisting essentially of" we mean containing no herbicides other than fenoxaprop and prodiamine, where unless otherwise specified the various adjuvants are optional. The emulsifible concentrate will advantageously 1) be stable, that is, not forming precipitates, within normal storage temperatures ranging from about freezing (0 or minus 15 C) to about 54 degrees C., for at least a month: 2) maintaining most (at least 80%, preferably at least 90%) of efficacy after a year of storage: and 3) be readily dispersible in normal agricultural water including moderately hard waters at the specified treatment concentrations.

Embodiments of the invention relate to a non-aqueous, emulsifiable concentrate formulation for improved herbicidal protection which consists essentially of
- (a) 10 weight percent to 33 weight percent, preferably 12 weight percent to 30 weight percent, more preferably between 15 weight percent to 25 weight percent weight percent of Prodiamine (99.4% active) herbicidal ingredient;
- (b) 2 weight percent to 10 weight percent, preferably 3 weight percent to 8 weight percent, more preferably between 3 weight percent to 6 weight percent weight percent of fenoxaprop-p-ethyl (98.5% active, "fenoxyprop") herbicidal ingredient;
- (c) 20 weight percent to 70 weight percent of a solvent selected from fatty acid dialkylamide solvents, gamma-butyrolactone, polar aprotic solvents, or mixtures thereof;
- (d) 1 weight percent to 6 weight percent, typically 2 weight percent to 5 weight percent of an alkyl-alkoxylate-based emulsifier, typically a alkyl-based EO-containing block copolymer emulsifier, for example an Ethylene oxide/Propylene oxide alkyl (e.g., butyl) block copolymer;
- (e) 0.5 weight percent to 5 weight percent of a hydrophilic non-ionic emulsifier, typically a ethoxylated fatty alcohol, for example a tridecyl alcohol hydrophilic non-ionic emulsifier; and
- (f) optionally, 0.1 to 5 weight percent of an anionic emulsifier, for example a fatty acid benzene sulfonate, particularly calcium salts of dodecylbenzenesulfonate.

The material is primarily intended as a once-per-season treatment of turf to control crabgrass. The amount of prodiamine in the various embodiments of the invention can vary, and is preferably greater than 15%, typically greater than 20%, for example from 15% to 33% by weight, or alternatively 20% to 33% by weight. Generally, the weight ratio of prodiamine to fenoxyprop is in the range 1:1 to 12:1, more typically 1:1 to 8:1, for example 3:1 to about 8:1, more preferably about 4:1 to about 6:1, or alternatively 1:1 to 3:1, for example about 5:1 or about 2:1. There must be sufficient fenoxyprop to effect a kill on existing crabgrass. The invention is another embodiment includes the application of the diluted emulsifiable concentrate, comprising or consisting essentially of prodiamine and fenoxyprop, to turf. The application timing and conditions of applying these herbicides are known in the art, and best efficacy of fenoxaprop is obtained by early application (before three tiller stage) and to well watered turf. Too much prodiamine, or too late an application of the diluted and dispersed aqueous composition, and the preemergent herbicide may interfere with fall over-seeding programs.

There are three different general embodiments of the emulsifiable concentrate of this invention. The first, a less preferred embodiment, has substantially no, e.g., less than 5% by weight, preferably less than 0.1% by weight, or no, polar aprotic solvents. Such an EC would be formulated with fatty acid dialkylamide solvents, gamma-butyrolactone, or both. Fatty acid dialkylamide solvents have excellent solvating power, in the range of 0.24 grams prodiamine per gram of solvent and 0.36 grams fenoxyprop per gram of solvent. Fatty acid dialkylamide solvents are "green" solvents, and can be readily utilized in making a non-aqueous, emulsifiable concentrate formulation for this invention. There is a wide variety of fatty acid dialkylamide solvents on the market, with the alkyl groups typically being a C1 to C3 alkyl group. Exemplary fatty acid amide solvents include N,N-dimethylcaprylamide (Cognis Agnique KE-3658) and N,N-dimethyloctanamide (Halcomid M8-10). Gamma-butyrolactone has excellent solvating power, in the range of 0.24 grams prodiamine per gram of solvent and 0.36 grams fenoxyprop per gram of solvent. Clearly, since on a weight basis there is preferably more prodiamine than fenoxyprop, and since prodiamine is less soluble in fatty acid amide solvents, the solubility of prodiamine will control. Such solvents are relatively expensive compared to certain aprotic solvents, and the solvating potential is only moderate compared to the preferred NMP solvent. This emulsifiable concentrate formulation which is (substantially) free of aprotic solvents is "green," but use in the absence of NPM will result in a practical limitation of about 10% to 15% prodiamine, with the amount of fenoxaprop being present in the weight ratio of prodiamine to fenoxyprop of 1:1 to 8:1, for example 2:1 to 6:1, or about 2:1, or alternatively 3:1 to about 8:1, more preferably about 4:1 to about 6:1, for example about 5:1. Such a formulation would be used to eliminate the modest concern over eye irritation that is inherent with polar aprotic solvents.

Preferred embodiments of the invention relate to a non-aqueous, emulsifiable concentrate formulation for improved herbicidal protection which comprise or consists essentially of
- a) 10 weight percent to 30 weight percent, preferably 12 weight percent to 25 weight percent, for example between 15 weight percent to 20 weight percent weight percent of Prodiamine (99.4% active) herbicidal ingredient;
- b) 2 weight percent to 10 weight percent, preferably 3 weight percent to 8 weight percent, more preferably between 3 weight percent to 6 weight percent weight percent of fenoxaprop-p-ethyl (98.5% active) herbicidal ingredient, or alternatively an amount of fenoxaprop so that the weight ratio of prodiamine to fenoxaprop is in the range of 2:1 to 8:1, for example 3:1 to about 8:1 or 1:1 to 3:1, more preferably about 4:1 to about 6:1, for example about 5:1;
- c) optionally but preferably 1 weight percent to 60 weight percent, typically 20 to 40 weight percent, total of a fatty acid dialkylamide solvent(s), gamma-butyrolactone, or both, wherein the presence of this solvent lowers the required amount of polar aprotic solvent;
- d) 20 weight percent to 60 weight percent, typically 20 weight percent to 40 weight percent of at least one polar aprotic organic solvent, for example wherein the polar aprotic organic solvent consists of, consists essentially of, or comprises an alkyl-2-pyrrolidinone, most preferably N,M-pyrrolidinone (N-Methyl-2-pyrrolidone, or "NMP"); and
- e) Other adjuvants, which may include
  - e1) 1 weight percent to 6 weight percent, typically 2 weight percent to 5 weight percent of an alkyl-alkoxylate-based emulsifier, typically a alkyl-based EO-containing block copolymer emulsifier, for example an Ethylene oxide/Propylene oxide alkyl (e.g., butyl) block copolymer;
  - e2) 0.5 weight percent to 5 weight percent of a hydrophilic non-ionic emulsifier, typically a ethoxylated fatty alcohol, for example a tridecyl alcohol hydrophilic non-ionic emulsifier; and
  - e3) optionally, 0.1 to 5 weight percent of an anionic emulsifier, for example a fatty acid benzene sulfonate, particularly calcium salts of dodecylbenzenesulfonate.

The third general class of embodiments comprises little or no, e.g., contains zero, or alternatively 0.1% to 20% by weight, or alternatively 0.1 to 10%, of a fatty acid dialkylamide solvent(s), gamma-butyrolactone, or both. The solvent system is primarily an aprotic solvent, preferably more than half of which is N,M-pyrrolidinone, and as a result the potential concentration of active ingredients is considerably higher than for other embodiments. Certain preferred embodiments of this aspect of the invention is an EC formulation for improved herbicidal protection which comprises or consists essentially of
- a) 10 weight percent to 33 weight percent, preferably 15 weight percent to 28 weight percent, more preferably between 20 weight percent to 26 weight percent weight percent of Prodiamine (99.4% active) herbicidal ingredient;
- b) 2 weight percent to 10 weight percent, preferably 3 weight percent to 8 weight percent, for example between 4 weight percent to 7 weight percent weight percent of fenoxaprop-p-ethyl (98.5% active) herbicidal ingredient, or alternatively an amount of fenoxaprop wherein the weight ratio of prodiamine to fenoxyprop is in the range of 1.5:1 to 8:1, typically 3:1 to about 8:1, more preferably about 4:1 to about 6:1, for example about 5:1 or about 2:1 to 2.5:1;
- c) optionally up to 20 weight percent, preferably less than 10 weight percent total of a fatty acid dialkylamide solvent(s), gamma-butyrolactone, or both;
- d) optionally 0 weight percent up to 20 weight percent, preferably less than 10 weight percent total of a heavy aromatic solvent naphtha, for example Solvesso® 150 or 200 solvent available from Exxon;
- e) 20 weight percent to 60 weight percent, typically 30 weight percent to 55 weight percent, of at least one polar aprotic organic solvent, for example wherein the polar aprotic organic solvent consists of, consists essentially of, or comprises alkyl-2-pyrrolidinones, most preferably N,M-pyrrolidinone, or for example in the embodiment where no fatty acid dialkylamide solvents, gamma-butyrolactone, or heavy aromatic solvent naphtha is present, a mixture of N,M-pyrrolidinone with other less water-soluble alkyl-pyrrolidinone, for example N-octyl-2-Pyrrolidone (e.g., AgsolEx 8 available from Ashland);
- f) Optionally 1 weight percent to 6 weight percent, typically 2 weight percent to 5 weight percent of an alkyl-alkoxylate-based emulsifier, typically a alkyl-based EO-containing block copolymer emulsifier, for example an Ethylene oxide/Propylene oxide alkyl (e.g., butyl) block copolymer;
- g) Optionally 0.5 weight percent to 5 weight percent of a hydrophilic non-ionic emulsifier, typically a ethoxylated fatty alcohol, for example a tridecyl alcohol hydrophilic non-ionic emulsifier; and
- h) optionally, 0.1 to 5 weight percent of an anionic emulsifier, for example a fatty acid benzene sulfonate, particularly calcium salts of dodecylbenzenesulfonate.

In this embodiment, use of N,M-pyrrolidinone alone, while it provides the greatest solubility for the active ingredients, is not suggested as the active ingredients may salt out when the EC is diluted with water. Alternatively, the heavy aromatic solvent naphtha can be used to prevent this salting out effect on dilution and dispersion of the EC into water.

We have found that a weight ratio of prodiamine to fenoxaprop of about 2:1, for example between 1:1 and 3:1 or between 1.5:1 to 2.5:1, provides surprisingly superior results in certain environments. Embodiments of this aspect of the invention is an EC formulation for improved herbicidal protection which comprises or consists essentially of:
- a) 15 weight percent to 25 weight percent, preferably 16 to 20 weight percent, of Prodiamine herbicidal ingredient;
- b) 5 weight percent to 14 weight percent, preferably 7 weight percent to 11 weight percent, of fenoxaprop-p-ethyl herbicidal ingredient; or alternatively an amount of fenoxaprop wherein the weight ratio of prodiamine to fenoxyprop is in the range of 1.5:1 to 2.5:1;
- c) 30 weight percent to 60 weight percent, typically 40 weight percent to 50 weight percent, of at least one polar aprotic organic solvent, for example wherein the polar aprotic organic solvent consists of, consists essentially of, or comprises alkyl-2-pyrrolidinones, most preferably N,M-pyrrolidinone, and/or less water-soluble alkyl-pyrrolidinone, for example N-octyl-2-Pyrrolidone;
- d) 10 weight percent to 30 weight percent, preferably 10 weight percent to 20 weight percent total of a fatty acid dialkylamide solvent(s), gamma-butyrolactone, a heavy aromatic solvent naphtha, for mixtures thereof, preferably fatty acid dialkylamide solvent(s);
- e) Optionally 2 weight percent to 10 weight percent, preferably 4 weight percent to 8 weight percent total, of emollients for example glycols, glycerine, or mixtures thereof;
- f) Optionally 0.5 weight percent to 5 weight percent, for example 2 weight percent to 3 weight percent, of a hydrophilic non-ionic emulsifier, typically an ethoxylated fatty alcohol or an ethoxylated fat, for example a tridecyl alcohol hydrophilic non-ionic emulsifier;
- g) Optionally 1 weight percent to 6 weight percent, typically 2 weight percent to 5 weight percent of an alkyl-alkoxylate-based emulsifier, typically a alkyl-based EO-containing block copolymer emulsifier, for example an Ethylene oxide/Propylene oxide alkyl (e.g., butyl) block copolymer, or alternatively an alkyl phenol polyoxyethylene glycol ether phosphate ester;
- h) f) Optionally 0.5 weight percent to 5 weight percent of an alkyl-alkoxylate-based emulsifier, typically a alkyl-based EO-containing block copolymer emulsifier, for example an Ethylene oxide/Propylene oxide alkyl (e.g., butyl) block copolymer or a castor oil ethoxylate.

In this last embodiment, items (f) an alkyl-alkoxylate-based emulsifier, (g) a hydrophilic non-ionic emulsifier, and (h) an anionic emulsifier, can be replaced with between 2 and 6 weight percent of Agent 3109-6 Proprietary Non-ionic Surfactant Blend available from Stepan.

In all of the embodiments, but especially in the third embodiment, inclusion of an effective amount of an emollient and of an antifreeze are recommended. Propylene glycol serves both purposes, and inclusion at an amount between 0.1 weight percent and 5 weight percent is beneficial. Glycerine and other known compounds are useful. In the third embodiment of the invention, with high concentrations of NMP, including more propylene glycol, for example up to 10% propylene glycol, can be beneficial.

In all of the embodiments, inclusion of 0.1 weight percent to 1.5 weight percent of a surfactant that can promote translocation of the herbicides is beneficial.

Generally, the amount of EC applied is contains the prodiamine in the amount necessary for season-long preemergent control. Crabgrass is an annual, and seeds form and germinate at an established date and then subsequently throughout the growing season. The amount of prodiamine needed to provide season-long control is known to those of skill in the art. In contrast to prodiamine, fenoxaprop is utilized and metabolized quickly, on the order of a week or so. The amount of prodiamine in the emulsifiable concentrate must be sufficient to provide the desired control. The weight ratio of fenoxaprop to prodiamine can vary from about 1:1 to about to about 1:12, but the preferred embodiments contain 3 parts to 6 parts prodiamine per part by weight of fenoxaprop. For early applications, greater amounts of prodiamine are preferred. For later applications, too much prodiamine can interfere with winter overseeding or reseeding. The amount of fenoxaprop must be effective. In tests of the instant co-formulations where insufficient season-long control was experienced, the mechanism is believed to be conditions where the crabgrass was sufficiently established, e.g., 4 tiller stage, coupled with environmental conditions such that the fenoxyprop did not kill established crabgrass, but rather knocked it back substantially, but which allowed regrowth.

Since the prodiamine is relatively stable, the initial treatment with the co-formulated emulsifiable concentrate should contain sufficient prodiamine to last throughout the growing season. Season-long effective control of crabgrass is expected with a single application, of for example by applying between 0.3 and 0.5 pounds of active prodiamine (in the EC of this invention, after dilution with water) per acre.

The prior art contains several tests wherein prodiamine and fenoxaprop provide synergistic results. While some efficacy data is presented here, the tests we "worst case" scenarios where crabgrass, often at the 4 tiller stage, covered a substantial fraction of the area of the test plots. The test conditions were such that only modest control was observed. The primary focus of the testing, however, was not relating to efficacy by rather to whether the formulations as applied would be phytotoxic to desired grasses. Generally, the herbicides as a granule, or as separate treatments, reduces phytotoxic effects. Treatment with a dispersed EC, which necessarily contains organic solvents, could promote phytotoxicity. In testing, however, using the preferred emulsifiable concentrates no phytotoxicity was observed.

DETAILED DESCRIPTION OF THE INVENTION

In the above descriptions, unless otherwise stated all ranges are weight percent, and the inclusion of multiple ranges should be construed as the inclusion of multiple lower limits and multiple upper limits, and different combinations of the upper and lower limits can be utilized than is presented.

It is an object of the present invention to produce a stable, low phytotoxic, environmentally friendly emulsifiable concentrate formulation of (comprising, consisting essentially of, or consisting of) prodiamine and fenoxaprop. Again, consisting essentially of means the only herbicidal agents in the emulsifiable concentrate are prodiamine and fenoxaprop. The more consistent application of active ingredient to turf utilizing an emulsifiable concentrate will provide for better pre-emergent efficacy and hence such EC's when applied can be expected to provide better coverage and effectiveness resulting in the potential lowering of herbicide loading on the environment. It is a further object of this invention to provide methods for controlling undesired weeds including especially crabgrass, by application to plants, of a herbicidally effective amount of the said EC formulation upon dilution with water. Yet another object of this invention is to provide a method to extend the application range and reduce the number of spraying for seasonal control of weeds such as crabgrass by the use of said EC formulation in general residential and commercial landscaped areas.

A final objective of this invention is to provide a method to spray on a formulation of Prodiamine and fenoxaprop onto urea and other fertilizer granules and achieve superior spreadability and distribution of the active herbicides than achievable by the use of SC or physical mixing with WDG formulations of Prodiamine and with fenoxaprop.

These and other objects and features of the invention will be more apparent from the specification set forth herein, and from the appended claims.

The following description is merely exemplary in nature and is not intended to limit the present disclosure, application, claims, compositions, or uses. While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

The aprotic solvent is preferably a pyrrolidone such as NMP, though one or more of dimethylsulfoxide (DMSO), dimethylformamide, and gamma-Butyrolactone alone or in mixtures, including mixtures with NMP, are useful. Various useful and incidental solvents are shown below, with the measured solubility of each of the active ingredients. The units for solubility below are grams of active ingredient per gram of respective solvent. All measurements were based on physical clarity and were performed at 22 degrees C.

| Solvent | Prodiamine | Fenoxaprop-p-ethyl |
|---|---|---|
| N-methyl pyrrolidinone (NMP) | 0.68 | 1.04 |
| Dimethylsulfoxide ("DMSO") | 0.24 | 0.72 |
| Aromatic 150 (Aromatic Naphtha Hydrocarbon) | 0.08 | 0.36 |
| Aromatic 200 (Aromatic Naphtha Hydrocarbon) | 0.07 | 0.24 |
| Glycol Ether EB (Diethylene glycol monubutyl ether) | 0.02 | 0.12 |
| Carbitol TM (Diethylene glycom monomethyl ether) | 0.01 | 0.12 |
| Jefsol 1555 Proprietary Solvent (Carbonate) | 0.004 | <0.12 |
| Glycol DPM (Dipropylene glycol methyl ether) | 0.008 | <0.12 |
| Halcomid M8-10 (fatty acid dialkylamide solvent) | 0.24 | 0.36 |
| Exxol D110 (Paraffin Hydrocarbon) | <0.02 | <0.04 |
| Agnique KE-3658 (fatty acid dialkylamide solvent) | 0.24 | 0.36 |
| BLO (Gamma-Butyrolactone) | 0.25 | 0.58 |
| DEGEE (Diethylene glycol monoethyl ether) | 0.05 | 0.08 |

It can be seen that each polar aprotic solvent, that is, NMP and DMSO, provide reasonable solubility, though NMP is far and away the superior solvent. NMP is water soluble, however, and a formulation of only NMP as the solvating agent runs the risk of salting out when the EC contacts water, as NMP solubility in water is appreciable. For example, dumping the EC into a tank containing residual water and then adding water can result in active ingredient forming a precipitate in the tank, which cannot be effectively applied to plants. Inclusion of a minor quantity, between 5% and 20% for example based on the weight of the NMP, of N-alkyl pyrrolidinones where the alkyl is C2 to C10 or preferably C6 to C8, or fatty acid dialkylamide solvents, or Aromatic Naphtha Hydrocarbon, can prevent this problem. If the amount of NMP in an EC is high, for example 50% by weight, then the EC further advantageously contains between 2.5% and 10% of one or more of higher alkyl pyrrolidinones, fatty acid dialkylamide solvents, Aromatic Naphtha Hydrocarbon, or mixture thereof. Said additions are useful for an EC with as little as 20% by weight NMP.

The aprotic solvent is the primary solvent in most embodiments of the EC. In one embodiment, there is little polar aprotic solvent, but such an EC has low concentration relative to other embodiments and is more useful for consumer use than for commercial use.

Preferred emulsifiable concentrates contain at least 15 weight percent to 28 weight percent, more preferably between 20 weight percent to 26 weight percent weight percent of Prodiamine (99.4% active) herbicidal ingredient, and sufficient fenoxaprop to provide a prodiamine to fenoxaprop ratio of between 1:1 to 12:1.

Polar organic solvents such as N-methypyrrolidone (NMP), dimethylformamide (DMF) and dimethylsulfoxide (DMSO) have been used to impart good solubility properties to a solvent mix but have environmental and phytotoxicity necessitating their reduction in formulations. Furthermore, there should not be any crystallization of the active compound from the EC for a reasonable period of time after water dilution and the EC itself should be physically and chemically stable during extended storage periods, under wide conditions. The emulsifiable concentrate can further incorporate various adjuvants to increase the efficacy of the formulation, provided that these must not disrupt the stability of the emulsion after water dilution.

While acetone might be useful for solvating the active ingredients, it is not included in the formulations because of its unfavorable vapor pressure and flash point.

Fatty amides, also called "fatty acid solvents" and fatty acid dialkylamide solvent(s) in this application, are amides formed from a fatty acid and an amine, of which many are known. Preferred are di-substituted fatty acid amides, which include as non-limiting examples N,N-dimethylcaprylamide (available from Cognis as Agnique™ KE-3658), and N,N-diethyloctanamide (available as Halcomid™ M8-10). These compounds can fully or partially replace aprotic solvents, and the solvating capacity approaches that of less-preferred aprotic solvents such as DMSO and gamma-Butyrolactone, that is, 0.24 to 0.25 grams prodiamine per gram solvent and greater amounts of fenoxaprop. A mixture of C8 and C10 fatty acid dimethylamide, (CAS 1118-92-9 and 14433-76-2) are useful.

The alkyl-alkoxylate-based emulsifier is typically an alkyl-based EO/PO-containing block copolymer emulsifier, for example an Ethylene oxide/Propylene oxide alkyl (e.g., butyl) block copolymer. It is possible to use suitable co-polymers of ethylene oxide and propylene oxide, such as ABA or BAB block copolymer or BA block copolymers. The alkyl group can range from C3 to C7, for example. A preferred group of ethylene oxide/propylene oxide block copolymers for use in the compositions of this invention are butyl based poly(oxypropylene)poly(oxyethylene) block copolymers having an average molecular weight in a range of 2.400 to 3.500 (e.g. TOXIMUL™ 8320, Stepan Chemical Co.) Also useful is Harcros™ TDA-12.

The hydrophilic non-ionic emulsifier can be a ethoxylated alcohol. A C9 to C18 alcohol can be used, with for example 8 to 20 EO units, for example a tridecyl alcohol hydrophilic non-ionic emulsifier. Examples include Makon™ TD-12, a tridecyl alcohol ethoxylate, POE-12 available from Stepan, or Harcros TDA-12.

Generally an anionic emulsifier can provide added emulsion stability, and alkyl sulfonates are useful for this purpose, for example a fatty acid benzene sulfonate. particularly calcium salts of dodecylbenzenesulfonate.

EXAMPLES

The following examples are provided for illustrative purposes only and are not limiting to this disclosure in any way. Indeed, various modifications of the invention, in addition to those shown and described herein, will become apparent to those skilled in the art from the following examples and the foregoing description. Such modifications are also intended to fall within the scope of the appended claims.

The following are exemplary emulsifiable concentrate formulations of prodiamine and fenoxaprop of the third general embodiment, where the solvent is primarily NMP, and wherein the weight ratio of prodiamine to fenoxaprop is about 4.3 to 1.

Sample 1000-e contained the following:

| Ingredients | % By Wt. | Description |
|---|---|---|
| Prodiamine Tech (99.36% A.I.) | 20.59 | ACTIVE |
| Fenoxaprop-P-Ethyl (98.5% A.I.) | 4.83 | ACTIVE |
| Mpyrol (NMP) | 59.6 | SOLVENT |
| Propylene Glycol | 10.0 | Anti-Freeze/emmolient |
| Agent 3109-6 | 5.0 | Surfactant blend |

Sample 1000-b contained the following:

| Ingredients | % By Wt. | Description |
|---|---|---|
| Prodiamine Tech (99.36% A.I.) | 20.59 | ACTIVE |
| Fenoxaprop-P-Ethyl (98.5% A.I.) | 4.83 | ACTIVE |
| Mpyrol (NMP) | 55.6 | SOLVENT |
| Agsolex 8 N-octyl-pyrrolidinone) | 4.0 | SOLVENT |
| Propylene Glycol | 10.0 | Anti-Freeze/emmolient |
| Agent 3109-6 | 5.000 | Surfactant blend |

Sample 1000-c contained the following:

| Ingredients | % By Wt. | Description |
|---|---|---|
| Prodiamine Tech (99.36% A.I.) | 20.59 | ACTIVE |
| Fenoxaprop-P-Ethyl (98.5% A.I.) | 4.83 | ACTIVE |
| Mpyrol (NMP) | 54.6 | SOLVENT |
| Solvesso 150 | 5.0 | SOLVENT |
| Propylene Glycol | 10.0 | Anti-Freeze/emmolient |
| Agent 3109-6 | 5.0 | Surfactant blend |

Sample 1000-d contained the following:

| Ingredients | % By Wt. | Description |
|---|---|---|
| Prodiamine Tech (99.36% A.I.) | 32.4 | ACTIVE |
| Fenoxaprop-P-Ethyl (98.5% A.I.) | 7.6 | ACTIVE |
| Mpyrol (NMP) | 53.0 | SOLVENT |
| Propylene Glycol | 5.0 | Anti-Freeze/emmolient |
| Agent 3109-6 | 2.0 | Surfactant blend |

Each of the above ECs of the third embodiment, containing high amounts of NMP and of active ingredients, formed clear to cloudy formulations.

In each case, we expect the proprietary surfactant blend can be replaced with the surfactants described in the example below.

Sample 1000-e, which is from the second general class of emulsifiable concentrates described in the Summary, and which was Slightly Hazy and formed an excellent emulsion, contained the following:

| Ingredients | % By Wt. | Description |
|---|---|---|
| Prodiamine Tech (99.36% A.I.) | 15.34 | ACTIVE |
| Fenoxaprop-P-Ethyl 98.5% A.I.) | 4.8 | ACTIVE |

-continued

| Ingredients | % By Wt. | Description |
|---|---|---|
| Agnique KE 3658 | 53.0 | SOLVENT |
| Mpyrol | 20.0 | SOLVENT |
| Toximul 8320 EO-PO butyl block copolymer | 3.0 | SURFACTANT |
| Agnique TDA-12 Tridecyl alcohol | 2.45 | SURFACTANT |
| Ninate 60 L, Calcium dodecylbenzenesulfonate, 60% linear | 1.4 | DISPERSANT |

The above composition was stable and dispersed readily when admixed with water. This Sample 1000-e was used in numerous efficacy tests and phytotoxicity tests described herein.

Not all formulations are successful, and below are a number of unsuccessful attempts.

Comparative example U had on ⅛" Crystals remaining in mixing vessel after 72 hrs. mixing

| Ingredients | % By Wt. |
|---|---|
| Prodiamine Tech (99.36% A.I.) | 16.9 |
| Fenoxaprop-P-Ethyl 98.5% A.I.) | 5.3 |
| Agnique KE 3658 | 50.93 |
| Mpyrol | 20.0 |
| Toximul 8320 | 3.0 |
| Agnique TDA-12 | 2.45 |
| Ninate 60 L | 1.4 |

Note this comparative example U was fairly close in composition to the sample 1000-e which was extensively field tested.

Comparative example V had on ¼" Crystals remaining in mixing vessel after 48 hrs. mixing.

| Ingredients | % By Wt. |
|---|---|
| Prodiamine Tech (99.36% A.I.) | 22.2 |
| Fenoxaprop-P-Ethyl 98.5% A.I.) | 7.3 |
| Agnique KE 3658 | 43.7 |
| Mpyrol | 20.0 |
| Toximul 8320 | 3.0 |
| Agnique TDA-12 | 2.45 |
| Ninate 60 L | 1.4 |

Comparative example Q had on ½" Crystals remaining in mixing vessel after 48 hrs. mixing.

| Ingredients | % By Wt. |
|---|---|
| Prodiamine Tech (99.36% A.I.) | 24.0 |
| Fenoxaprop-P-Ethyl 98.5% A.I) | 7.5 |
| Agnique KE 3658 | 41.65 |
| Mpyrol | 20.0 |
| Toximul 8320 | 3.0 |
| Agnique TDA-12 | 2.45 |
| Ninate 60 L | 1.4 |

Comparative example Q had on ½" Crystals remaining in mixing vessel after 48 hrs. mixing.

| Ingredients | % By Wt. |
|---|---|
| Prodiamine Tech (99.36% A.I.) | 25.2 |
| Fenoxaprop-P-Ethyl 98.5% A.I.) | 8.0 |
| Agnique KE 3658 | 39.93 |
| Mpyrol | 20.0 |
| Toximul 8320 | 3.0 |
| Agnique TDA-12 | 2.45 |
| Ninate 60 L | 1.4 |

Using between 40 and 55% fatty acid dialkylamide solvents, and only 20% NMP, resulted in an EC containing only 15.34% prodiamine and 4.8% fenoxaprop. While this was lower concentration than desired, the formulation proved useful and stable. Field tests were performed on this Sample 1000-e (labeled "PA-1000" in the test reports), and after a year of storage further tests are ongoing.

Various embodiments of the formulations disclosed herein, when formulated into a herbicidal composition, show a surprising and unexpected performance in efficacy and low phytotoxicity for general residential and commercial landscaped herbicide treatment as well as for direct application to urea and other fertilizers for superior pre-emergence weed control.

To demonstrate this activity, a series of trials were performed and are described below. In all tests, Sample 1000-e described above is labeled as PA-1000. The formulations tested were:

| Formulation No | % Active Ingredient(s) | Fl oz/A | lb ai/A |
|---|---|---|---|
| PA-1000 | 15.24% prodiamine + 4.76% fenoxaprop | 32 | 0.31 + 0.097 |
| PA-1000 | 15.24% prodiamine + 4.76% fenoxaprop | 40 | 0.39 + 0.122 |
| PA-1000 | 15.24% prodiamine + 4.76% fenoxaprop | 50 | 0.48 + 0.152 |
| Comp PA-1010 | 15.4% prodiamine | 40 | 0.39 |
| Comp PA-1020 | 6.59% fenoxaprop (Acclaim Extra) | 27.4 | 0.122 |

Test #1 Initiated: May 1, 2012 (1-3 tiller stage) on a mix of *Digitaria ischaemum* and *D. sanguinalis*—smooth and large crabgrass. Summary Comments: Very good initial knockdown and control of crabgrass (14 DAT), however by 56 DAT there was a rebound of crabgrass in the treated plots and control was unacceptable. The % Crabgrass Control for 14, 28, 56, and 84 Days After Treatment (DAT) are shown below.

| | | % Crabgrass Control Days After Treatment (DAT) | | | |
|---|---|---|---|---|---|
| Formulation No. | Fl oz/A | 14 | 28 | 56 | 84 |
| PA-1000 | 32 | 80 | 70 | 21 | 11 |
| PA-1000 | 40 | 85 | 83 | 36 | 17 |
| PA-1000 | 50 | 87 | 77 | 37 | 19 |
| PA-1010 | 40 | 17 | 21 | 6 | -4 |
| PA-1020 | 27.4 | 83 | 72 | 25 | -4 |
| Untreated | xxx | 0 | 0 | 0 | 0 |

Field test #2: Test #2 Initiated: Aug. 1, 2012 (1-3 tiller stage) on a mix of *Digitaria ischaemum* and *D. sanguinalis*—smooth and large crabgrass). Summary Comments: At equal lb ai/A fenoxaprop-ethyl rates the co-formulation (PA-1000) provided numerically better crabgrass control than the corresponding rate of Acclaim Extra (PA-1020), however the level of crabgrass control was commercially unacceptable for all treatments (maximum of 69% control). The % Crabgrass Control for 14 and 28 Days After Treatment (DAT) are shown below.

| Formulation No. | Fl oz/A | lb ai/A | 14 | 28 |
|---|---|---|---|---|
| PA-1000 | 40 | 0.122 | 50 | 69 |
| PA-1000 | 50 | 0.173 | 14 | 37 |
| PA-1020 | 28 | 0.122 | 23 | 19 |
| PA-1020 | 39 | 0.173 | −14 | 19 |
| Untreated | xxx | xxx | 0 | 0 |

Field test #3: Field test June 2012 was conducted at the Landscape Horticulture Research Center at the University Of Illinois⌐—Urbana/Champaign in Urbana, Ill. Treatments were applied to a mature stand of Kentucky bluegrass L.cv. 'Bewitched' maintained at a 0.875-inch height of cut. The experimental design used was a randomized complete block with four replications and plots measured 4×6 feet. Treatments were applied with a backpack-type CO2 sprayer at 32 PSI fitted with VS8002 nozzles (TeeJet Technologies, Wheaton, Ill.) and a spray volume of 50 gallons acre-1. Treatments were applied on Jun. 27, 2012. Test #3 Initiated: Jun. 27, 2012 (1-3 tiller stage; *Digitaria ischaemum*, smooth crabgrass) Summary Comments: PA-1000 (40 and 50 fl oz/A) and PA-1020 treatments provided good postemergence control of crabgrass at the 29 days after application reading date. After 56 days crabgrass control held up from PA 1000 treatments, however, the control from Comp Ex. PA-1020 dropped from 3 to 69% control. The % Crabgrass Control for 29 and 56 Days After Treatment (DAT) are shown below.

| Formulation No. | Fl oz/A | | 29 | 56 |
|---|---|---|---|---|
| PA-1000 | 32 | | 74 | 73 |
| PA-1000 | 40 | | 91 | 89 |
| PA-1000 | 50 | | 86 | 88 |
| PA-1010 | 40 | | 0 | 0 |
| PA-1020 | 27.4 | | 83 | 69 |
| Untreated | xxx | [% Crabgrass Density] | 26 | 49 |

Field test May 2012 by Southeastern Turfgrass Research & Consulting, LLC evaluated phytotoxicity at a field between a pond and trees in Lexington Ky. Tall fescue at 3.5 inches was in 44 Sand, 48% silt, 8% clay, OM: 3.9 Loam with a CEC of 9.4 and a pH of 6.1. Fertilizer level was poor. Application was by CO2 sprayer at 30 psi. applying 40 fl. Oz. per acre of PA-1000 on May 24, 2012. The test showed minor differences in turf quality at day 15 between treated and untreated, and results were identical between treated and untreated on days 21 and 28 after treatment.

Test #1 Initiated: May 24, 2012 (1-3 tiller stage—primarily *Digitaria ischaemum*, smooth crabgrass, with some large crabgrass (*D. sanguinalis*). Summary Comments: Poor initial activity on crabgrass (15 DA-A) was obtained from the fenoxaprop-ethyl component of the co-formulation (PA-1000) as well as Acclaim Extra (PA-1020). Control increased by 28 DA-A, however, the crabgrass rebounded and control was unacceptable at 56 DA-A. The % Crabgrass Control for 15, 28, 56 and 81 Days After Treatment (DAT) are shown below.

| Formulation No. | Fl oz/A | 15 | 28 | 56 | 81 |
|---|---|---|---|---|---|
| PA-1000 | 40 | 36 | 91 | 26 | 1 |
| PA-1000 | 50 | 31 | 79 | 32 | 9 |
| PA-1010 | 40 | 28 | 34 | 0 | 0 |
| PA-1020 | 27.4 | 31 | 64 | 20 | 0 |
| Untreated | % Crabgrass | [59] | [69] | [90] | [94] |

Test #2 Initiated: Jul. 23, 2012 (1-3 tiller stage—primarily *Digitaria sanguinalis*, large crabgrass, with some smooth crabgrass (*D. ischaemum*). Summary Comments: Initial crabgrass control (15 DA-A) and observations so far up to 35 DA-A show very good activity from the fenoxaprop-ethyl component of PA-1000 and PA-1020. This is much different than what was observed in the first test that was initiated on May 24 to crabgrass of similar size. The % Crabgrass Control for 15, 21 and 35 Days After Treatment (DAT) are shown below.

| Formulation No. | Fl oz/A | | 15 | 21 | 35 |
|---|---|---|---|---|---|
| PA-1000 | 32 | | 97 | 92 | 90 |
| PA-1000 | 40 | | 96 | 95 | 93 |
| PA-1000 | 50 | | 94 | 90 | 88 |
| PA-1010 | 40 | | 0 | 0 | 0 |
| PA-1020 | 27.4 | | 94 | 94 | 95 |
| Untreated | xxx | [% Crabgrass] | [60] | [65] | [70 |

Virginia Tech University (Dr. Shawn Askew/Angela Post). Test #1 (65-12) initiated: May 30, 2012 (1-3 tiller stage—*Digitalia ischaemum*, smooth crabgrass). Summary Comments: Starting from a low level of crabgrass at test initiation (5.0-6.5% cover), PA-1000 and PA-1020 provided a high level of control up to the 7-week reading (51 days after application). Crabgrass control fell at the 12-week reading (81 days after application) with PA-1000 providing percent crabgrass control from the mid-70's to mid-80's, while PA-1020 fell to 62.5% control. The % Crabgrass Control for 9, 16, 26 and 51 Days After Treatment (DAT) are shown below.

| Formulation No. | Fl oz/A | 0 | 9 | 16 | 26 | 51 |
|---|---|---|---|---|---|---|
| PA-1000 | 40 | [6.5] | 100 | 100 | 100 | 100 |
| PA-1000 | 50 | [6.5] | 100 | 100 | 100 | 100 |
| PA-1010 | 40 | [5.8] | 0 | 0 | 0 | 0 |
| PA-1020 | 27.4 | [5.0] | 100 | 100 | 99.5 | 100 |
| Untreated | xxx | 5.8% Crabgrass Cover | ?? | [7.5] | [35] | [70] |

Virginia Tech University (Dr. Shawn Askew/Angela Post). Test #2 (66-12) initiated: May 25, 2012 (1-3 tiller stage—*Digitaria ischaemum*; smooth crabgrass). Summary Comments: A moderate level of crabgrass was present at test initiation (16.3-25% cover). Crabgrass control held up well through 8 weeks (56 days after application) for both the PA-1000 and PA-1020 treatments. At 12.5 weeks after test initiation, crabgrass control fell to 73.8-87.5% for PA-1000 and to a substantially lower 47.1% control for the PA-1020 product. The % Crabgrass Control for 14, 21, 31 56 and 87 Days After Treatment (DAT) are shown below.

| Formulation No. | Fl oz/A | 0 | 14 | 21 | 31 | 56 | 87 |
|---|---|---|---|---|---|---|---|
| PA-1000 | 32 | [22.5] | 100 | 100 | 99.5 | 100 | 73.8 |
| PA-1000 | 40 | [16.3] | 100 | 100 | 99.5 | 100 | 87.5 |
| PA-1000 | 50 | [23.8] | 100 | 100 | 99.3 | 100 | 81.8 |
| PA-1010 | 40 | [25.0] | 0 | 0 | 0 | 0 | 0 |
| PA-1020 | 27.4 | [23.8] | 100 | 100 | 100 | 100 | 47.1 |
| Untreated | % Control | [23.8] | ?? | 23.8 | 43.8 | 72.5 | 100 |

Rutgers University (Dr. Steve Hart/Carrie Mansue). Test Initiated: Jun. 27, 2012 (1-3 tiller stage—*Digitaria sanguinalis;* large crabgrass). Summary Comments: At test initiation mean percent crabgrass cover ranged from 28.8-

41.3% for the treatments. At 14 days after application moderate crabgrass injury was noted from the PA-1000 and PA-1020 formulations, but this did not translate to good crabgrass control as after 29 days post-treatment, the three rates of PA-1000 only provided 33-51% crabgrass control and PA-1020 showed higher crabgrass populations than at test initiation. The % Crabgrass Control for 29, 42, and 71 Days After Treatment (DAT) are shown below.

| Formulation No. | Fl oz/A | | Days After Application | | | |
|---|---|---|---|---|---|---|
| | | | 0 | 29 | 42 | 71 |
| PA-1000 | 3 | | [28.8] | 38 | 0 | 0 |
| PA-1000 | 4 | | [41.3] | 33 | 0 | 0 |
| PA-1000 | 5 | | [35.0] | 51 | 0 | 0 |
| PA-1010 | 4 | | [38.8] | 0 | 0 | 0 |
| PA-1020 | 27.4 | [% Crabgrass | [35.0] | 0 | 0 | 0 |
| Untreated | xxx | Cover] | [30.0] | [60] | [90] | [87.5] |

Additionally, at 14 days after treatment crabgrass injury was recorded, 38%, 36%, 42%, 5%, 36%, and 0% respectively for the runs in the above table.

University of Massachusetts (Dr. Prasanta Bhowmik). Test initiated: Jun. 7, 2012 (1-3 tiller stage—*Digitaria sanguinalis*, large crabgrass). Summary Comments: Very high population of crabgrass at test initiation (>90%). Initial burndown of crabgrass from fenoxaprop-ethyl in the co-formulation as well as in Acclaim Extra (PA-1020) at 13 days-after-application was good. Note that Bhowmik also added to this test his own treatments of Acclaim Extra as well as Drive XLR8. Crabgrass control from PA-1000 was fair to good at the 21 and 28 days-after-application reading dates, however, it fell after this period. Bhowmik. The % Crabgrass Control for 4, 4, and 13 days After Treatment (DAT) are shown below.

| Formulation No. | Fl oz/A | | 0 | 4 | 7 | 13 |
|---|---|---|---|---|---|---|
| | | (crabgrass burndown) | | (crabgrass control) | | |
| PA-1000 | 32 | [90.0] | 0 | 48.8 | 97 | 93.8 |
| PA-1000 | 40 | [93.8] | 7.5 | 66.3 | 99.5 | 97 |
| PA-1000 | 50 | [95.0] | 22.5 | 70 | 100 | 92.5 |
| PA-1010 | 40 | [93.8] | 7.5 | 0 | 0 | 0 |
| PA-1020 | 27.4 | [96.3] | 2.5 | 65 | 99 | 95.8 |
| Untreated | [% Crab Cover] | [98.8] | 0 | 0 | 0 | 0 |
| Drive XLR8 | 65.34 | [92.5] | 93.8 | 94.5 | 99 | 98.3 |
| Acclaim Extra | 27.8 | [95.0] | 28.8 | 60 | 74 | 70 |

Field test April 2012 performed at Southeastern Turfgrass Research & Consulting, LLC (Lexington, Ky.) to evaluate phytotoxicity on a stand of well-managed lawn-height tall fescue turf. Tall fescue (Barrington/Barlexas/Barvado tall fescue blend by Barenbrug) at 3.5" lawn mowing height was treated on Jul. 23, 2012. PA-1000 was applied at 32, 40, 64 and 96 fl. Oz. per acre. No phytotoxicity was observed at any rating period, which were 6, 15, 21, and 28 days after treatment. Turfgrass quality, where 1=brown, dead turf and 9=perfect green turf, was 6.5 to 6.8 for the treated plots at day 6 versus 6.8 for untreated control. At days 20 and 26 after treatment, turfgrass quality was identical between treated and untreated blocks, measuring 7.0 in all cases.

Field test March 2012 was conducted to test if application of PA-1000 results in phytotoxicity to desired cool season turfgrasses. The turf species tested was Kentucky bluegrass (*Poa pratensis*) that had a small amount of perennial ryegrass (*Lolium perenne*). The study was conducted at The Ohio Turfgrass Foundation Research and Education Center in Columbus, Ohio. The sites of the experiment was weed-free. Individual treatment plots were 3'6 ft and there were treatments and an untreated control (Table 1). The experimental design was a randomized complete block with 3 replications. The experiments were all established on Jun. 5, 2012. PA-1000 was applied at 32, 40, 64 and 96 fl. Oz. per acre. A backpack carbon dioxide sprayer equipped with 6503 nozzles with a spray pressure of 40 psi was used to apply the products with the equivalent of 2 gal H2O/1000 ft2. Turfgrass phytotoxicity data were collected at 7, 14, and 28 days after application of treatments (DAT) by visually estimating percent injury to the turfgrass on a scale of 0 to 10 with 0=no injury and 10=dead turfgrass. The data were analyzed using the General Linear Models procedure of SAS. Fishers protected LSD was conducted on the data.

Barely noticeable injury symptoms were noted in all treated plots at 7 DAT. This was primarily a very light chlorosis. However, none of the differences were statistically significant. The rates tested caused no injury significantly different than the untreated plots at 14 DAT. At 28 DAT no phytotoxicity was noted. Finally, though the rating for plots treated with treatment 4 was numerically lower, there were no significant quality differences observed at 43 DAT. PA-1010 was safe to Kentucky bluegrass at all rates tested. Treated and control blocks showed 0.3 damage at day 7 and 0.0 damage at days 14 and 28, where zero is no damage and 10 is dead turf. Turf quality for both treated and untreated was rated 7.0 at 43 days after testing.

| Trt | Product | Rate | 7 | 14 | 28 | 43 Quality‡ |
|---|---|---|---|---|---|---|
| | | | Turfgrass Phytotoxicity (0-10)† | | | |
| 1 | PA-1000 | 32 | 1.0 | 0.3b¶ | 0 | 7.3 |
| 2 | PA-1000 | 40 | 1.3 | 0.3b | 0 | 7.7 |
| 3 | PA-1000 | 64 | 1.0 | 0.7b | 0 | 7.0 |
| 4 | PA-1000 | 96 | 1.7 | 1.7a | 0 | 6.7 |
| 5 | PA-1010 | 40 | 0.3 | 0.0b | 0 | 7.0 |
| 6 | PA-1020 | 27.4 | 1.3 | 0.3b | 0 | 7.3 |
| 7 | Untreated | | 0.3 | 0.0b | 0 | 7.0 |
| LSD$_{(0.05)}$ | | | NS$_\S$ | 0.9 | — | NS |

†Turfgrass phytotoxicity rated on a 0-10 scale where 0 = no damage and 10 = dead turf
‡Turfgrass Quality rated on a 1-9 scale where 1 = dead turf, 6 = minimum acceptable quality and 9 = perfect Field test January 2012 evaluated turfgrass phytotoxicity using the Example 4 (Table 4) formulation. The test was performed by Virginia Tech University (Blacksburg, Va.), TEST #63-12, on Kentucky bluegrass (Midnight) at 0.6" fairway mowing height in an irrigated site with irrigation received as needed. The grass was treated May 29, 2012. No injury to Midnight Ky bluegrass observed throughout the study (28 days). No significant differences in % turfgrass cover were noted compared to the untreated control 28 days after the test was initiated. PA-1000 was applied at 32, 40, 64 and 96 fl. Oz. per acre.

No significant differences in % turfgrass cover were noted compared to the untreated control 28 days after the test was initiated.

| Formulation No. | Fl oz/A | Turfgrass Injury (%) | | | % Turfgrass Cover | |
|---|---|---|---|---|---|---|
| | | Days After Application (DA-A) | | | | |
| | | 9 | 17 | 28 | 0 | 28 |
| PA-1000 | 32 | 0 | 0 | 0 | 73.8 a | 71.3 a |
| PA-1000 | 40 | 0 | 0 | 0 | 72.5 a | 72.5 a |
| PA-1000 | 64 | 0 | 0 | 0 | 67.5 a | 72.5 a |

-continued

| Formulation No. | Fl oz/A | Turfgrass Injury (%) Days After Application (DA-A) | | | % Turfgrass Cover Days After Application (DA-A) | |
|---|---|---|---|---|---|---|
| | | 9 | 17 | 28 | 0 | 28 |
| PA-1000 | 96 | 0 | 0 | 0 | 67.5 a | 73.8 a |
| PA-1010 | 40 | 0 | 0 | 0 | 71.3 a | 61.3 a |
| PA-1020 | 27.4 | 0 | 0 | 0 | 72.5 a | 76.3 a |
| Untreated | xxx | 0 | 0 | 0 | 77.5 a | 68.8 a |

There was no statistically significant difference between the treated blocks and the control.

Field test February 2012 evaluated turfgrass phytotoxicity using the Example 4 (Table 4) formulation. The test was performed by Virginia Tech University (Blacksburg, Va.), TEST #64-12, on Perennial ryegrass (ASP6004) at 0.6" fairway mowing height in an irrigated site with irrigation received as needed. The grass was treated May 29, 2012. PA-1000 was applied at 32, 40, 64 and 96 fl. Oz. per acre. No injury to Perennial ryegrass observed throughout the study (28 days). No significant differences in % turfgrass cover were noted compared to the untreated control 28 days after the test was initiated.

| Formulation No. | Fl oz/A | Turfgrass Injury Days After Application (DA-A) | | | Turfgrass Cover Days After Application (DA-A) | |
|---|---|---|---|---|---|---|
| | | 10 | 17 | 28 | 0 | 28 |
| PA-1000 | 32 | 0 | 0 | 0 | 73.8 a | 62.5 a |
| PA-1000 | 40 | 0 | 0 | 0 | 76.3 | 67.5 a |
| PA-1000 | 64 | 0 | 0 | 0 | 67.5 a | 57.5 a |
| PA-1000 | 96 | 0 | 0 | 0 | 71.3 a | 71.3 a |
| PA-1010 | 40 | 0 | 0 | 0 | 72.5 a | 65 a |
| PA-1020 | 27.4 | 0 | 0 | 0 | 70 a | 63.8 a |
| Untreated | xxx | 0 | 0 | 0 | 72.5 a | 63.8 a |

There was no statistically significant difference between the treated blocks and the control.

Field test June 2012 was conducted at the Landscape Horticulture Research Center at the University Of Illinois¬—Urbana/Champaign in Urbana, Ill. Treatments were applied to a mature stand of Kentucky bluegrass L.cv. 'Bewitched' maintained at a 0.875-inch height of cut. The experimental design used was a randomized complete block with four replications and plots measured 4×6 feet. Treatments were applied with a backpack-type CO2 sprayer at 32 PSI fitted with VS8002 nozzles (TeeJet Technologies, Wheaton, Ill.) and a spray volume of 50 gallons acre-1. Treatments were applied on Jun. 27, 2012. PA-1000 was applied at 32, 40, 64 and 96 fl. Oz. per acre.

The lowest rate of PA-1000.32 fl oz/A, was not different than the untreated turf. By 4 WAT. No significant differences in Kentucky Bluegrass injury were apparent. A Rating for turf density and quality was taken on July 16th at 19DAT. As the rate of PA-1000 Increased from 32 to 96 fl oz/A, turf quality decreased. Turf density was similarly reduced as PA-1000 Rate increased. This Trial shows that PA-1000 can significantly injure Kentucky bluegrass at higher application rates and care must be exercised when choosing a rate of this herbicide for use on Kentucky bluegrass. This trial represented a worse case scenario for herbicide injury since it is started just prior to the onset of extremely warm temperatures including four Kentucky bluegrass injury was rated on a scale of 0-10 with 0=none and 10=dead turf. Kentucky bluegrass quality was rated on a scale of 1-9 where, 1=low and 9=high quality. Kentucky bluegrass density was rated on a scale of 1-9 where, 1=open, 6=typical normal density and 9=very dense. This study experienced record breaking high temperatures during the first 2 weeks of the trial. The first eleven days of the trial had 5 days over 90 and 6 days at or over 100 degrees F. The average high temperature for the first eleven days was 98.5 F! No phytotoxicity was observed and treated plots showed higher quality and density than untreated control.

The above examples are exemplary and are not meant to limit the invention.

What is claimed:

1. An emulsifiable concentrate for herbicidal protection which comprises:
   a) 10 weight percent to 33 weight percent of Prodiamine herbicidal ingredient;
   b) 2 weight percent to 10 weight percent of fenoxaprop-p-ethyl herbicidal ingredient; and
   c) 20 weight percent to 70 weight percent of a solvent selected from fatty acid dialkylamide solvents, gamma-butyrolactone, polar aprotic solvents, or mixtures thereof;
   d) 1 weight percent to 6 weight percent of an alkyl-alkoxylate-based emulsifier; and
   e) 0.5 weight percent to 5 percent of a hydrophilic nonionic emulsifier, wherein the weight ratio of prodiamine to fenoxaprop-p-ethyl is between 1:1 and 12:1, and wherein there are no other herbicidal ingredients in the emulsifiable concentrate.

2. The emulsifiable concentrate of claim 1, said emulsifiable concentrate further comprising 0.1 to 5 weight percent of an anionic emulsifier.

3. The emulsifiable concentrate of claim 1, said emulsifiable concentrate comprising at 12 weight percent to 25 weight percent prodiamine, wherein the weight ratio of prodiamine to fenoxaprop-p-ethyl is between 1:1 and 3:1.

4. The emulsifiable concentrate of claim 1, said emulsifiable concentrate comprising at 12 weight percent to 25 weight percent prodiamine, wherein the weight ratio of prodiamine to fenoxaprop-p-ethyl is between 3:1 and 8:1.

5. The emulsifiable concentrate of claim 1, said emulsifiable concentrate comprising 20 weight percent to 60 weight percent of alkyl-2-pyrrolidinones.

6. The emulsifiable concentrate of claim 1, said emulsifiable concentrate comprising 20 weight percent to 60 weight percent of N,M-pyrrolidinone and between 2.5% and 10% of one or more of N-alkyl pyrrolidinones where the alkyl is C2 to C10, fatty acid dialkylamide solvents, Aromatic Naphtha Hydrocarbon, or mixture thereof.

7. The emulsifiable concentrate of claim 1, said emulsifiable concentrate comprising greater than 15% by weight prodiamine, wherein the weight ratio of prodiamine to fenoxaprop-p-ethyl is between 1:1 and 3:1.

8. The emulsifiable concentrate of claim 1, said emulsifiable concentrate comprising greater than 20% by weight prodiamine, wherein the weight ratio of prodiamine to fenoxaprop-p-ethyl is between 1:1 and 3:1.

9. The emulsifiable concentrate of claim 1, said emulsifiable concentrate comprising greater than 20% by weight prodiamine, wherein the weight ratio of prodiamine to fenoxaprop-p-ethyl is between 3:1 and 8:1.

10. A non-aqueous, emulsifiable concentrate which comprises:
   a) 10 weight percent to 30 weight percent of Prodiamine herbicidal ingredient;
   b) 2 weight percent to 10 weight percent of fenoxaprop-p-ethyl herbicidal ingredient;

c) 1 weight percent to 60 weight percent total of a fatty acid dialkylamide solvent(s), gamma-butyrolactone, or mixture thereof;
d) 20 weight percent to 60 weight percent of at least one polar aprotic solvent;
e) 1 weight percent to 6 weight percent of an alkyl-alkoxylate-based emulsifier; and
f) 0.5 weight percent to 5 weight percent of a hydrophilic non-ionic emulsifier; wherein the emulsifiable concentrate contains no other herbicidal ingredient.

11. The non-aqueous, emulsifiable concentrate of claim 10 wherein the polar aprotic solvent is N-methylpyrrolidinone.

12. The non-aqueous, emulsifiable concentrate of claim 10 wherein the weight ratio of prodiamine to fenoxaprop-p-ethyl is between 1:1 and 3:1.

13. The non-aqueous, emulsifiable concentrate of claim 10 wherein the weight ratio of prodiamine to fenoxaprop-p-ethyl is 2:1.

14. The non-aqueous, emulsifiable concentrate of claim 10 wherein the weight ratio of prodiamine to fenoxaprop-p-ethyl is between 3:1 and 8:1.

15. A non-aqueous, emulsifiable concentrate formulation which consists essentially of:
a) 15 weight percent to 25 weight percent of Prodiamine herbicidal ingredient;
b) 5 weight percent to 14 weight percent of fenoxaprop-p-ethyl herbicidal ingredient;
c) 30 weight percent to 60 weight percent of at least one polar aprotic organic solvent, wherein the polar aprotic organic solvent comprises at least one alkyl-2-pyrrolidinone;
d) 10 weight percent to 30 weight percent of a fatty acid dialkylamide solvents,
e) optionally 2 weight percent to 10 weight percent of emollients;
f) 1 weight percent to 6 weight percent of an alkyl-alkoxylate-based emulsifier;
g) 0.5 weight percent to 5 weight percent of a hydrophilic non-ionic emulsifier; and
h) optionally, 0.1 to 5 weight percent of an anionic emulsifier, wherein there are no other herbicidal ingredients in the emulsifiable concentrate.

16. The non-aqueous, emulsifiable concentrate of claim 15 wherein the weight ratio of prodiamine to fenoxaprop-p-ethyl is between 3:1 and 8:1.

17. The non-aqueous, emulsifiable concentrate of claim 15 wherein the weight ratio of prodiamine to fenoxaprop-p-ethyl is between 1:1 and 3:1.

18. A method of treating turf comprising mixing an emulsifiable concentrate of claim 1 with water, and applying an effective amount of the diluted emulsifiable concentrate to turf.

* * * * *